United States Patent [19]

Baccala et al.

[11] Patent Number: 4,785,810
[45] Date of Patent: Nov. 22, 1988

[54] INTRAOCULAR LENS FOLDING AND INSERTION APPARATUS

[75] Inventors: Vincent J. Baccala; Charles A. Bonte, Sr., both of St. Louis, Mo.

[73] Assignee: Storz Instrument Company, St. Louis, Mo.

[21] Appl. No.: 918,711

[22] Filed: Oct. 14, 1986

[51] Int. Cl.⁴ .............................................. A61B 17/28
[52] U.S. Cl. ................. 128/321; 128/303 R; 623/6
[58] Field of Search ............... 128/303 R, 321; 623/6

[56] References Cited

U.S. PATENT DOCUMENTS

| | | | |
|---|---|---|---|
| 2,253,132 | 8/1941 | Malson | 128/321 |
| 2,631,585 | 3/1953 | Siebrandt | 128/321 |
| 2,698,483 | 1/1955 | Berkowitz | 128/321 |
| 2,743,726 | 5/1956 | Grieshaber | 128/321 |
| 3,040,746 | 6/1962 | Chester | 128/321 |
| 3,209,753 | 10/1965 | Hawkins et al. | 128/321 |
| 3,589,369 | 6/1971 | Alksnis | 128/321 |
| 4,024,870 | 5/1977 | Sandel | 128/321 |
| 4,122,556 | 10/1978 | Poler | |
| 4,143,427 | 3/1979 | Anis | |
| 4,170,043 | 10/1979 | Knight et al. | |
| 4,190,049 | 2/1980 | Hager et al. | |
| 4,198,980 | 4/1980 | Clark | |
| 4,214,585 | 8/1980 | Bailey, Jr. | |
| 4,325,375 | 4/1982 | Nevyas | 128/321 |
| 4,429,421 | 2/1984 | Levy | |
| 4,484,911 | 11/1984 | Berlin et al. | 128/346 |
| 4,527,294 | 8/1985 | Heslin | |
| 4,530,117 | 8/1985 | Kelman | |
| 4,573,998 | 3/1986 | Mazzocco | |

OTHER PUBLICATIONS

The Surgical Armamentarium, Instruments and Equipment, p. 878, 1980.

Primary Examiner—C. Fred Rosenbaum
Assistant Examiner—Gene B. Kartchner
Attorney, Agent, or Firm—Harness, Dickey & Pierce

[57] ABSTRACT

A lens folding and insertion apparatus for use in insertion of an intraocular lens through an incision in an eye. The lens folding and insertion apparatus includes a lens folding jaw arrangement having a first trough shaped jaw and a second rod shaped jaw which hingedly folds an intraocular lens upon itself into a U-shaped configuration.

11 Claims, 1 Drawing Sheet

INTRAOCULAR LENS FOLDING AND INSERTION APPARATUS

TECHNICAL FIELD

The present invention relates to surgical instruments used in replacement of the natural lenses in eyes with artificial lenses. More specifically, the present invention relates to an intraocular lens folding and inserting apparatus to be used with intraocular lenses having foldable optical zone portions which can be implanted in eyes through small incisions.

BACKGROUND ART

It is common today to remove natural lenses which have been clouded with cataracts and implant artificial intraocular lenses in the eye substantially restoring the sight of the individual. In order to remove the cataractous natural lens of the eye and replace it with an intraocular lens, the integrity of the eye cavity must be breached. Eye surgery of this type is of a very sensitive nature, it requires incisions in corneal tissues and interior portions of the eye and may optically or otherwise affect the vision of the patient. It is advantageous when performing this surgery to use the smallest corneal incision possible which will allow the surgeon to accomplish the task of removing the necessary portions of the natural lens and insert a replacement intraocular lens. Generally, a smaller incision in the corneal tissue will create less trauma to the eye and reduce the possibility of post surgical complications.

The procedure for removal of the natural lens of the eye can be accomplished by the use of a relatively small incision. However, the implanting of intraocular lens implants of the past have required the use of a larger incision in the corneal tissue in order to allow the lens to pass through and be positioned in the posterior or anterior chamber of the eye.

Intraocular lenses of the past have generally been designed with a non-deformable lens body and flexible fixation elements extending from it which center and hold the lens in position in the eye. The incision necessary to insert such intraocular lenses is generally determined by the diameter of the nondeformable lens body of the implant (which typically is on the order of 6-8 mm in diameter). The fixation elements are normally flexible and can be folded over the lens body during insertion, or the lens implant can be rotated through the insertion.

More recently, lenses have been produced which have deformable optical zones and fixation elements which are deformed and inserted through a smaller incision in the ocular tissue of an eye and which will return to their original shape upon insertion into the eye. An example of lenses of this type is shown in U.S. Pat. No. 4,573,998, issued to Mazzocco. Typically, these foldable intraocular lenses are made from a silicone material.

Past apparatuses for insertion of intraocular lenses have included various instruments for holding of the lenses and inserting them through incisions into the eye. Instruments used for this purpose have ranged from common forceps, to configurations specifically designed to engage and hold a particular intraocular lens design for inserting the lens through the incision into the operative position in the posterior or anterior chambers of the eye. Examples of such prior art devices may be found in U.S. Pat. Nos. 4,122,556; 4,143,427; 4,170,043; 4,190,049; 4,198,980; 4,214,585; 4,429,421; 4,527,294; and 4,530,117.

Some apparatuses for insertion of deformable intraocular lenses are disclosed in the Mazzocco patent, U.S. Pat. No. 4,573,998. As disclosed therein, the deformable lenses may be deformed to smaller sizes by pulling or pushing them through incisions in the cornea by a hook-like tool, by sucking the lens through small openings in syringe-type tool, or by folding, rolling, or crushing the lenses into non-distinct shapes by the instruments as set forth therein. While these apparatuses and instruments may allow deformation and insertion of deformable intraocular lenses through small incisions in the eye, they have disadvantages in that they may damage the integrity of the lens implants or may release the lens implants in an undesirable or unknown position in the interior of the eye.

For instance, the hooking or otherwise pushing or stretching of the lens implant through the incision may cause damage to or tearing of the lens implant at the point of engagement between the hook and the edge of the lens. The use of a syringe arrangement may allow the lens implant to be released into the eye in any number of unknown positions, many of which may be undesirable and may require further entrance into the internal chambers of the eye to adjust the positioning of the lens implant. The forceps-type designs disclosed require compression of the lens into non-descript folded shapes which may damage the lens implant at creases in the folds. These creases may cause optical deformations in the lens and may even require further surgery to alleviate these problems. In addition, the apparatuses disclosed may cause problems in the releasing of the intraocular lens after the instrument is inserted into the eye cavity.

SUMMARY OF INVENTION

The present invention provides a lens folding and insertion apparatus or instrument for use in insertion of an intraocular lens through an incision in an eye, the apparatus comprising a folding means for folding an intraocular lens upon itself into a defined "U" shape. The folding means comprises jaw means for folding the intraocular lens. The jaw means have opened and closed positions and are operable to fold the intraocular lens in the closed position.

It is an object of the present invention to allow a deformable intraocular lens to be accurately positioned through a relatively small incision in the eye cavity. It is a further object of the present invention to provide a lens folding and insertion apparatus which does not cause damage to the intraocular lens implant. It is a further object of the present invention to provide a lens folding and insertion apparatus which will not cause any undue stress or sharp creases in the lens implant which might reduce the quality of vision through the lens implant or create ocular deformities in the lens implant which could reduce accurate vision through the lens implant.

A still further object of the present invention is to provide a lens folding and insertion apparatus which securely holds an intraocular lens implant in a known position providing for more accurate placement of the lens in the anterior or posterior chamber of the eye. It is a further object of the present invention to provide a lens folding and insertion apparatus which provides minimal deforming of the lens implant and still provides for substantial reduction in size of the intraocular lens implant.

Other objects, purposes, features and advantages of the invention will become apparent to those skilled in the art when the following description and claims are reviewed. The present invention is also described with greater specificity and clarity in the attached drawings which are described below.

DESCRIPTION OF THE PREFERRED EMBODIMENTS

Figures 1, 2, 3:
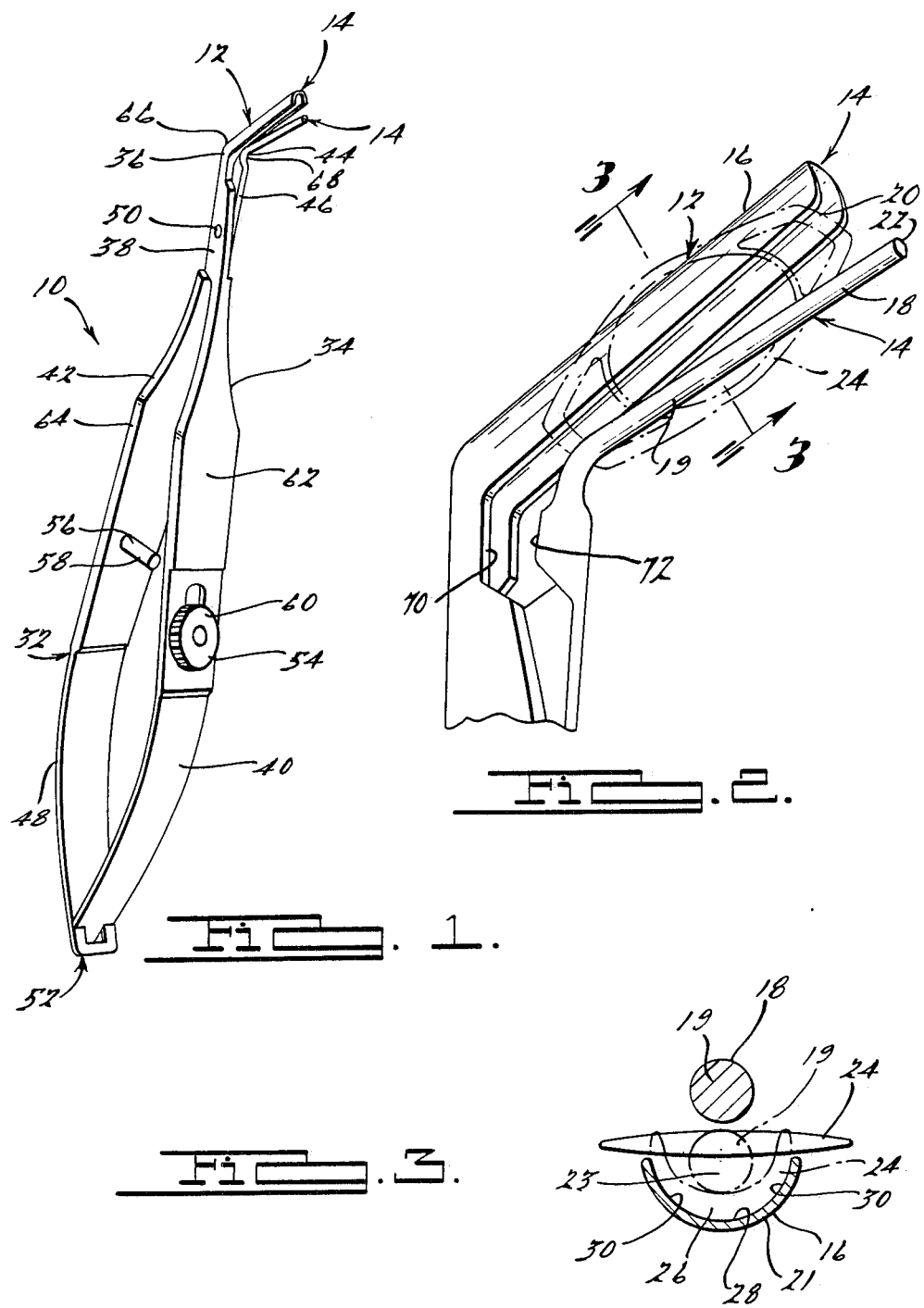
FIG. 1 is a perspective view of the lens folding and insertion apparatus of the present invention.
FIG. 2 is an enlarged perspective view of the jaws of the lens folding and insertion apparatus of the present invention.
FIG. 3 is a cross-sectional view of the jaws of the present invention taken along line 3—3 in FIG. 2 (and in direction of the arrows 3—3), and depicting the side of the instrument with a foldable lens.

As seen in FIG. 1, the present invention comprises a lens folding and insertion apparatus, generally indicated at 10, for use in insertion of an intraocular lens in an incision in an eye. The lens folding and insertion apparatus of the present invention consists of folding means, generally shown at 12, for folding an intraocular lens upon itself.

The folding means 12 of the present invention further comprises jaw means, generally shown at 14. The jaw means 14 of the present invention has an open position and a closed position. As shown in FIGS. 1 and 2, the jaw means is in the open position. In operation of the apparatus, the intraocular lens implant is folded upon itself when the jaw means 14 engages the intraocular lens in the closed position (as shown in phantom lines in FIG. 3).

Referring now to FIG. 2, the jaw means 14 includes a first jaw memer 16 and a second jaw member 18. The first jaw member 16 has a circular hollowed out portion 20 and the second jaw member has an engaging portion 22. The engaging portion 22 operatively engages intraocular lens 24 within hollowed out portion 20 and thereby folds the intraocular lens 24 into a U-shape when the jaw means is in the closed position, as illustrated in FIG. 3.

As illustrated in FIG. 3, the hollowed out portion 20 of the first jaw member preferably is an elongated concave surface and the engaging surface 22 is an elongated convex surface. Preferably the elongated convex surface 22 substantially parallels the elongated concave surface 20 and defines a lens folding space 26 between elongated concave surface 20 and elongated convex surface 22 when the jaw members are in the closed position as shown in FIG. 3. The hollowed out portion 20 may be an elongated opening with a semi-circular cross section 21 and the engaging portion 22 is an elongated member which has a circular cross section 23. The diameter of the semi-circular cross section 21 of first jaw member 16 is greater than the diameter of the circular cross section 23 of the engaging portion 22 such that when the jaw members come together in parallel engagement, the lens folding space 26 is defined.

In a preferred embodiment of the invention, as shown in FIG. 1, the hollowed out portion 20 of first jaw member 16 comprises an elongated U-shaped trough which has a circular bottom 28 and parallel side portions 30 which define the trough. The engaging portion 22 of the preferred embodiment, namely second jaw member 18, comprises a rod member 19 which has a circular cross section. The elongated U-shaped trough defined by circular bottom 28 and sides 30, has a width which is greater than the diameter of the circular cross section of the rod member 19. More specifically in the preferred embodiment, the outside diameter of the second jaw member of the preferred embodiment is 0.020 inches, and the width of the elongated U-shaped trough of lower jaw member 18 is 0.090 inches. Thus, when first jaw member 16 and second jaw member 18 are in the closed position, as shown in FIG. 3 the rod member 19 is operatively positioned in the elongated U-shaped trough and defines a lens folding space 26 between the surfaces of the rod member and the elongated U-shaped trough. The exemplary jaw members 16 and 18 preferably include surfaces 70 and 72 at their respective lower portions, which engage one another in the closed position in order to substantially prevent full engagement of the rod member 19 and the U-shaped trough and maintain the lens folding space 26 in the closed position. While the sides are described as generally parallel they can be of any configuration such as being turned in towards each other which would provide for folding or curling of the lens in a "U" shaped or circular configuration.

A forcep means, generally shown at 32, is provided for actuating first jaw member 16 and second jaw member 18 between the open and closed positions. Forcep means 32 is operated such that the first jaw member 16 and the second jaw member 18 are aligned in axial parallel position when they are closed.

The forcep means 32 of the present invention comprises a first handle means 34 which includes a first jaw end 36 forming the first jaw member 16, and has a first pivotal portion 38 and a first biasing end 40. The forcep means 32 also includes a second handle means 42 including a second jaw end 44 for forming the second jaw member 18, a second pivotal portion 46 and a second biasing end 48. The first handle means 34 and the second handle means 42 are operatively connected at the first pivotal portion and the second pivotal portion (38 and 46, respectively) by screw 50 such that when arms 34 and 42 are moved toward each other, the jaw members are moved toward the closed position (FIG. 3). The forceps means 32 also includes biasing means generally shown at 52 for biasing the first jaw member and the second jaw member toward the open position by biasing separation of the first biasing end 40 and the second biasing end 48. The biasing means of the present invention may include any configuration which operates to bias the first handle means 34 and the second handle means 42 apart from each other. In the preferred embodiment of the present invention, the biasing means includes arcuate spring arm portions 40 and 48 which are made of spring-type metal and biased apart from each other by the arcuate shape of the arms.

A locking means 54 may be used in the present invention for selectively locking the first handle means 34 to the second handle means when the first jaw member 16 and second jaw member 18 are in their closed positions. The locking means 54 further comprises a locking pin 56 on the second handle means 42 which includes a locking slot 58. A sliding lock 60 is provided on the first handle means 34 for slidably engaging the locking slot 58 and holding the apparatus in the closed position. The lock as shown in the Figures and as used in the present invention is a "barraquer" lock and stop arrangement, which is readily known to those skilled in the art. This type of locking arrangement allows for the adjustable locking and stopping of the jaws when they are in the closed position such that the present apparatus may be used for lenses having variable cross-sectional widths. The handle means 34 and 42 include the first and second actuation arms, 62 and 64, respectively. In the preferred embodiment of the invention, the first jaw member 16 and the second jaw member 18 are formed at obtuse angles to their corresponding first 62 or second 64 actuation arms. The obtuse angle is preferably between 90° to 180°. More preferably, the obtuse angle is from between about 120° to about 150°, and most preferably the angle is about 130°.

While a forceps arrangements is preferably used in the present invention, any other arrangement whereby the first jaw member and second jaw member are brought together in a substantially parallel aligned configuration could be used without deviating from the scope of the present invention.

Thus in the preferred embodiment of the present invention, a lens folding and insertion apparatus 10 is provided for use in the insertion of an intraocular lens 22 through an incision in an eye. The lens folding and insertion apparatus 10 of the preferred embodiment comprises a first elongated jaw member 16 having a U-shaped cross section 20 and a second elongated jaw member 18 having a generally circular cross section.

A first actuation arm 62 is connected to the first elongated jaw 16 at an angle of about 130° at a first angled portion 66. A second actuation arm 64 is provided and is connected to the second elongated jaw 18 and forms an angle of about 130° at a second angled portion 68. The first actuation arm 62 crosses and is pivotally connected to the second actuation arm 64 at pivotal screw 50 which is in a direction away from the first 16 and second 18 elongated jaws and at a point slightly away from the first angled portions 66 and second angled portions 68, thus providing for hinged engaging alignment of the first elongated jaw 16 with the second elongated jaw 18.

The first and second elongated jaw members have an open position as shown in FIG. 1 and a closed position as shown in FIG. 3. The first and second elongated jaws hingedly come together in the closed position and define lens folding space 26 for folding an intraoclar lens upon itself in a "U" shaped configuration. The lens folding space 26 is formed between the U-shaped space in the first elongated jaw 16 and the outer periphery of the second elongated jaw 18. The second elongated jaw 18 has a circular cross sectional diameter such that the second elongated jaw 18 is substantially enveloped within the U-shaped space 20 of the first elongated jaw 16 in the closed position (FIG. 3). The first actuation arm 62 has a first biasing portion 40 and the second actuation arm 64 has a second biasing portion 48. The first biasing portion and the second biasing portion (40 and 48, respectively) are operatively attached (52) at the end opposite of the first and second elongated jaws (16, 18, respectively) and bias the first 16 and second 18 elongated jaws toward the open position (FIG. 1). The second actuation arm includes locking pin 56 having locking slot 58 extending from the second actuation arm toward the first actuation arm 62. The first actuation arm includes an adjustable sliding lock 60 for engaging the locking slot 58 and holding the apparatus in the closed position, and for adjustable positioning of the first and second elongated jaws (16, 18, respectively) in the closed position.

In operation, an intraocular lens 24 is positioned between the first 16 and second 18 elongated jaw members when they are in their open position. The intraocular lens 24 is folded upon itself in a "U" or "taco shell" type shape by actuation of the first and second actuation arms towards one another and thereby folding the intraocular lens 24 into the lens folding space 26. As shown by the dashed outline of lens 24 in FIG. 2, preferably the lens 24 is folded in half lengthwise, i.e. the haptic portions are positioned in line with the lengths of the jaws and actuation arms, although it is also possible to fold the lens widthwise. The jaw members holding the intraocular lens 24 are then inserted into the anterior or posterior chamber of the eye, whichever is desired, through an incision in the eye. With the present invention, it is possible to use an incision of about 3–4 mm in width, rather than 6–8 mm which had to be used with nondeformable or rigid intraocular lenses. The locking mechanism is released when the lens is in the appropriate position and the intraocular lens implant is allowed to unfold into its primary shape and be positioned in the eye.

The present invention is advantageous for use with a deformable intraocular lens with memory characteristics such as those disclosed in Mazzocco U.S. Pat. No. 4,573,998. As disclosed in that patent, the intraocular lens can be made from a polyurethane elastomer, silicone elastomer, hydrogel polymer collagen compounds, organic or synthetic gel compounds or combinations thereof. However, the apparatus can be used with any intraocular lens implant which is resilient enough to be folded in an U-shaped configuration for insertion through an incision in the eye, without deviating from the scope of the present invention.

The foregoing discussion discloses and describes merely exemplary embodiments of the present invention. One skilled in the art will readiliy recognize from such discussion that various changes, modifications, and variations may be made therein without departing from the spirit and scope of the invention as defined in the following claims.

What is claimed is:

1. A lens folding and insertion apparatus for use in eye surgery for insertion of an intraocular lens through an incision of approximately 3 to 4 millimeters in an eye, said lens folding and insertion apparatus comprising:

forceps means having a first elongated jaw member and a second elongated jaw member, said forceps means having means for actuating said first jaw member and said second jaw member into open and closed positions, said first jaw member including a substantially smooth elongated concave surface and said second jaw member having a substantially smooth elongated convex surface, said first jaw member and said second jaw member being in operable alignment wherein said first jaw member and said second jaw member are actuated toward one another into said closed position with the intraocular lens positioned between said first jaw member, and said second jaw member, said first jaw member and said second jaw member folding the intraocular lens upon itself by engagement between said elongated concave surface and said elongated convex surface, said elongated concave surface defining an open generally U-shaped elongated trough having lateral side edges and a circular bottom, and said second jaw member being a rod having a circular cross-section defining said convex surface, the lateral width of said elongated trough being substantially greater than the diameter of said circular cross-section of said rod, said rod being aligned within said elongated trough and disposed laterally between said lateral side edges when in said closed position, said forcep means including means for substantially preventing full engagement of said rod and said elongated trough in order to define a lens folding space between said rod and said elongated trough when said jaw members are in said closed position, and the diameter of said rod being sufficiently small relative to the depth of said elongated trough such that at least one-half of the diameter of said rod is disposed within said trough when said jaw members are in said closed position with the intraocular lens therebetween in said lens folding space in order to allow the intraocular lens to be gripped, folded and inserted into the approximately 3 to 4 millimeter incision in the eye.

2. An apparatus according to claim 1 wherein said forceps means further comprises a pair of actuation arms each having a biasing end, a pivot point and attenuating into said first jaw member and said second jaw member, said actuation arms crossing and operably attached at said pivot points in such a way that movement of said actuation arms toward one another causes movement of said jaw members toward said closed position, said biasing ends having biasing means for biasing said pair of actuation arms apart toward said open position.

3. An apparatus according to claim 2 wherein said first jaw member is formed at an obtuse angle with one of said actuation arms an said second jaw member is formed at said obtuse angle with the other of said actuation arms.

4. An apparatus according to claim 3 wherein said obtuse angle is between 90°–180°.

5. An apparatus according to claim 3 wherein said obtuse angle is between 110° to 150°.

6. An apparatus according to claim 3 wherein said obtuse angle is about 130°.

7. An apparatus according to claim 2 wherein said pair of actuation arms include a locking means for locking said first jaw member and said second jaw member in said closed position.

8. An apparatus according to claim 7 wherein said locking means comprises adjustment means for adjusting said lens folding space defined by said first jaw member and said second jaw member in said closed position.

9. An apparatus according to claim 7 wherein said locking means further comprises a locking pin having a locking slot, extending between said pair of actuating arms from one of said actuation arms and a sliding lock on the other of said actuation arms for slidably engaging said locking slot and holding said apparatus in said closed position.

10. An apparatus according to claim 9 wherein said sliding lock further comprises screwable adjustment means for adjustable locking engagement of the lens folding space between said first and said second jaw members.

11. An apparatus according to claim 1, wherein the outside diameter of said circular second jaw member is less than 0.025 inch, and the width of said U-shaped trough is less than 0.10 inch, in order to allow for insertion and manipulation of said apparatus and the gripped and folded intraocular lens in said approximately 3 to 4 millimeter incision in the eye.

* * * * *